US012575739B2

(12) United States Patent
Gaubert et al.

(10) Patent No.: US 12,575,739 B2
(45) Date of Patent: Mar. 17, 2026

(54) DISTRIBUTED SENSOR NETWORK FOR MEASUREMENT OF BIOMETRIC PARAMETER

(71) Applicant: Apple Inc., Cupertino, CA (US)

(72) Inventors: Zachary Gaubert, Austin, TX (US); Jacky G. Ko, Sunnyvale, CA (US); Han Bi, Santa Clara, CA (US); Saahil Mehra, Brookline, MA (US); Sinan Filiz, San Mateo, CA (US); Xinsheng Chu, Saratoga, CA (US); Adriaan J. Taal, Mountainview, CA (US)

(73) Assignee: Apple Inc., Cupertino, CA (US)

( * ) Notice: Subject to any disclaimer, the term of this patent is extended or adjusted under 35 U.S.C. 154(b) by 685 days.

(21) Appl. No.: 17/947,823

(22) Filed: Sep. 19, 2022

(65) Prior Publication Data

US 2023/0085860 A1 Mar. 23, 2023

Related U.S. Application Data

(60) Provisional application No. 63/246,735, filed on Sep. 21, 2021.

(51) Int. Cl.
*A61B 5/01* (2006.01)
*A61B 5/00* (2006.01)
(52) U.S. Cl.
CPC ................ *A61B 5/01* (2013.01); *A61B 5/681* (2013.01); *A61B 5/7267* (2013.01); *A61B 5/742* (2013.01);
(Continued)
(58) Field of Classification Search
CPC ......... A61B 5/01; A61B 5/681; A61B 5/7267; A61B 5/742; A61B 5/7203; A61B 2562/0271; A61B 2562/04
See application file for complete search history.

(56) References Cited

U.S. PATENT DOCUMENTS

| | | | |
|---|---|---|---|
| 4,935,345 A | 6/1990 | Guilbeau | |
| 5,623,594 A | 4/1997 | Swamy | |
| (Continued) | | | |

FOREIGN PATENT DOCUMENTS

| | | | |
|---|---|---|---|
| CA | 2654084 | 12/2007 | |
| CN | 2136464 Y | 6/1993 | |
| (Continued) | | | |

OTHER PUBLICATIONS

Maurer et al., "eWatch: a wearable sensor and notification platform," International Workshop on Wearable and Implantable Body Sensor Networks (BSN'06), Apr. 3-5, 2006, 4 pages.

(Continued)

*Primary Examiner* — Eric F Winakur
*Assistant Examiner* — Sienna C Pyle
(74) *Attorney, Agent, or Firm* — Brownstein Hyatt Farber Schreck, LLP

(57) ABSTRACT

One embodiment described herein takes the form of a wearable electronic device, such as a watch, including a housing, a memory and a processor located in the housing, and three or more sensors. Each sensor of the three or more sensors is configured to generate a measurement of a parameter. Each sensor of the three or more sensors is located in a different region in the housing. The processor is configured to execute instructions stored in the memory. In response to execution of the instructions by the processor, the processor is configured to generate an adjusted measurement of the biometric parameter using at least the measurements of the parameter generated by the three or more sensors. The parameter is a temperature, and the biometric parameter is a body temperature of a user.

17 Claims, 7 Drawing Sheets

(52) U.S. Cl.
CPC ..... *A61B 5/7203* (2013.01); *A61B 2562/0271*
(2013.01); *A61B 2562/04* (2013.01)

(56) References Cited

U.S. PATENT DOCUMENTS

| | | |
|---|---|---|
| 6,639,395 B2 | 10/2003 | Male |
| 6,741,470 B2 | 5/2004 | Isenburg |
| 7,299,090 B2 | 11/2007 | Koch |
| 7,416,332 B2 | 8/2008 | Rountree et al. |
| 7,479,116 B2 | 1/2009 | Yarden et al. |
| 7,622,896 B2 | 11/2009 | Nakagawa |
| 7,649,439 B2 | 1/2010 | Thomsen, III |
| 7,852,710 B2 | 12/2010 | Kelly et al. |
| 8,292,495 B2 | 10/2012 | Bieberich et al. |
| 8,292,502 B2 | 10/2012 | Bieberich et al. |
| 8,304,851 B2 | 11/2012 | Trifonov |
| 8,550,702 B2 | 10/2013 | Campbell et al. |
| 8,617,381 B2 | 12/2013 | Sun et al. |
| 8,649,998 B2 | 2/2014 | Yarden et al. |
| 8,954,288 B2 | 2/2015 | Aljabari |
| 9,300,157 B2 | 3/2016 | Bergqvist et al. |
| 9,304,520 B2 | 4/2016 | Cheng |
| 9,326,097 B2 | 4/2016 | Sen et al. |
| 9,438,071 B1 | 9/2016 | Heiberg |
| 9,562,869 B2 | 2/2017 | Mueller et al. |
| 9,599,520 B2 | 3/2017 | Angeli et al. |
| 9,671,296 B2 | 6/2017 | Niederberger et al. |
| 9,733,130 B2 | 8/2017 | Blundell |
| 9,976,914 B2 | 5/2018 | Radhakrishnan et al. |
| 9,990,172 B2 | 6/2018 | Komaromi et al. |
| 9,993,178 B2 | 6/2018 | Panescu et al. |
| 10,151,527 B2 | 12/2018 | Rusnack et al. |
| 10,197,457 B2 | 2/2019 | Jang et al. |
| 10,238,301 B2 | 3/2019 | Weebadde et al. |
| 10,244,985 B1 | 4/2019 | Sayani et al. |
| 10,309,840 B2 | 6/2019 | Kalyanasundaram |
| 10,371,584 B2 | 8/2019 | Kim et al. |
| 10,500,087 B2 | 12/2019 | Thomas et al. |
| 10,553,179 B2 | 2/2020 | Holenarsipur et al. |
| 10,713,461 B2 | 7/2020 | Benkley, III |
| 10,750,951 B1 | 8/2020 | Prachar |
| 10,827,931 B2 | 11/2020 | Meyerson et al. |
| 10,852,277 B2 | 12/2020 | Takagi et al. |
| 10,987,054 B2 | 4/2021 | Pandya et al. |
| 11,224,344 B2 | 1/2022 | Ellis et al. |
| 11,253,157 B2 | 2/2022 | Tanaka et al. |
| 11,406,268 B2 | 8/2022 | Tsuchimoto |
| 11,408,778 B2 | 8/2022 | Clements et al. |
| 11,419,549 B2 | 8/2022 | Shimuta |
| 11,519,875 B2 | 12/2022 | Strandberg et al. |
| 11,557,709 B2 | 1/2023 | Martinis |
| 2005/0139250 A1 | 6/2005 | DeSteese et al. |
| 2005/0257822 A1 | 11/2005 | Smith et al. |
| 2007/0290532 A1 | 12/2007 | Frank |
| 2008/0234004 A1 | 9/2008 | Loque et al. |
| 2010/0245090 A1 | 9/2010 | Smith et al. |
| 2011/0119018 A1 | 5/2011 | Skarp |
| 2011/0245713 A1 | 10/2011 | Rensen et al. |
| 2012/0128024 A1 | 5/2012 | Tsuchida et al. |
| 2014/0163765 A1 | 6/2014 | Jain et al. |
| 2014/0241399 A1 | 8/2014 | Rud |
| 2015/0016487 A1 | 1/2015 | Britton et al. |
| 2016/0058375 A1 | 3/2016 | Rothkopf et al. |
| 2017/0007167 A1 | 1/2017 | Kostic et al. |
| 2017/0288452 A1 | 10/2017 | Adams et al. |
| 2018/0004169 A1 | 1/2018 | Matsuzaki et al. |
| 2018/0028072 A1 | 2/2018 | Shi |
| 2018/0206729 A1 | 7/2018 | Wang et al. |
| 2019/0175024 A1 | 6/2019 | Lan et al. |
| 2019/0309204 A1 | 10/2019 | Takagi et al. |
| 2019/0377304 A1 | 12/2019 | Zhong et al. |
| 2021/0089168 A1 | 3/2021 | Patel et al. |
| 2021/0121071 A1 | 4/2021 | Mensch et al. |
| 2021/0186336 A1 | 6/2021 | Bellifemine et al. |
| 2021/0264346 A1 | 8/2021 | Momayez et al. |
| 2021/0278290 A1 | 9/2021 | Ghoreyshi et al. |
| 2021/0404883 A1 | 12/2021 | Rahmani et al. |
| 2022/0000370 A1 | 1/2022 | Blom et al. |
| 2022/0087534 A1 | 3/2022 | Mansky et al. |
| 2022/0330422 A1 | 10/2022 | Lemire |
| 2022/0373404 A1 | 11/2022 | Clements et al. |
| 2022/0377930 A1 | 11/2022 | Morimoto et al. |
| 2022/0386878 A1 * | 12/2022 | Li ........................... G01J 5/064 |
| 2023/0093738 A1 | 3/2023 | Ko et al. |
| 2023/0414108 A1 * | 12/2023 | Lee ..................... A61B 5/0008 |

FOREIGN PATENT DOCUMENTS

| | | | |
|---|---|---|---|
| CN | 101548881 | 10/2009 | |
| CN | 103873636 | 6/2014 | |
| CN | 104006895 | 8/2014 | |
| CN | 104204749 | 12/2014 | |
| CN | 205121417 | 3/2016 | |
| CN | 107145253 | 9/2017 | |
| CN | 108871609 | 11/2018 | |
| CN | 109245325 | 1/2019 | |
| CN | 106706167 | 5/2019 | |
| CN | 110520873 | 11/2019 | |
| CN | 110546491 | 12/2019 | |
| CN | 112444322 | 3/2021 | |
| DE | 29922560 | 3/2000 | |
| DE | 10358791 | 8/2005 | |
| DE | 102009003848 | 11/2010 | |
| JP | 2005091045 | 4/2005 | |
| JP | 2012132818 | 7/2012 | |
| KR | 20180097191 | 8/2018 | |
| WO | WO 13/185679 | 12/2013 | |
| WO | WO 18/152566 | 8/2018 | |
| WO | WO-2020206372 A1 * | 10/2020 | ........... A61B 5/0008 |
| WO | WO 20/249665 | 12/2020 | |
| WO | WO-2022137895 A1 * | 6/2022 | ........... G01J 5/0025 |

OTHER PUBLICATIONS

Sim, Jai K. et al: Thin film resistance temperature detector array for the measurement of temperature distribution inside a phantom. In. Metrologia, vol. 55, 2017. DOI 10.1088/1681-7575/aa90bd, 9 pages.

Bangchao, Yang et al.; "Multi chip module MCM technology and its application;" University of Electronic Science and Technology Press; Aug. 31, 2001; pp. 430-431.

* cited by examiner

400a

| DETERMINE IMPACT OF CONDITION(S) ON SKIN TEMPERATURE | ~402 |

| DETERMINE SKIN TEMPERATURE | ~404 |

| ADJUST DETERMINED SKIN TEMPERATURE BASED ON THE DETERMINED IMPACT OF CONDITION(S) ON SKIN TEMPERATURE | ~406 |

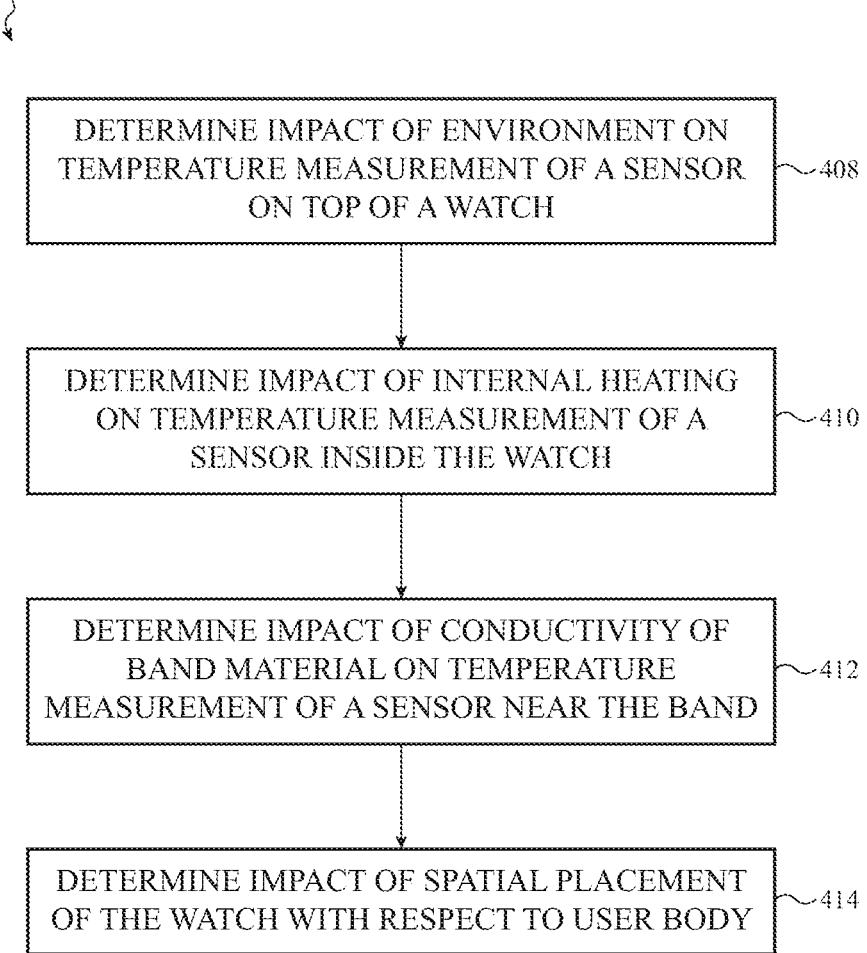

400b

DETERMINE IMPACT OF ENVIRONMENT ON TEMPERATURE MEASUREMENT OF A SENSOR ON TOP OF A WATCH ~408

DETERMINE IMPACT OF INTERNAL HEATING ON TEMPERATURE MEASUREMENT OF A SENSOR INSIDE THE WATCH ~410

DETERMINE IMPACT OF CONDUCTIVITY OF BAND MATERIAL ON TEMPERATURE MEASUREMENT OF A SENSOR NEAR THE BAND ~412

DETERMINE IMPACT OF SPATIAL PLACEMENT OF THE WATCH WITH RESPECT TO USER BODY ~414

*FIG. 4B*

DISTRIBUTED SENSOR NETWORK FOR MEASUREMENT OF BIOMETRIC PARAMETER

CROSS-REFERENCE TO RELATED APPLICATION

This application is a nonprovisional patent application and claims the benefit under 35 U.S.C. § 119(e) of U.S. Provisional Patent Application No. 63/246,735, filed on Sep. 21, 2021, the content of which is incorporated herein by reference for all purposes.

TECHNICAL FIELD

Embodiments described herein generally relate to electronic devices for measuring a biometric parameter.

BACKGROUND

Currently available wearable electronic devices offer various health monitoring features, such as temperature measurement, heart rate measurement, and so on. In some cases, temperature measurements may be used to predict ovulation of a female user of the wearable electronic device. In some cases, temperature measurements may be used to predict whether a user is well or sick, or to help in the assessment of various health conditions affecting the cardiovascular system or other bodily systems. In some cases, a device may have a temperature sensor located at a place that is likely to be in constant contact, or near-constant contact, with a user's skin.

SUMMARY

Embodiments described herein generally relate to electronic devices having a network of distributed sensors for measuring a biometric parameter. More particularly, various embodiments described herein take the form of a wearable electronic device, such as a watch, having a number of sensors, particularly three or more sensors. The three or more sensors may be configured to measure a biometric parameter, such as a temperature of a user of the wearable electronic device.

One embodiment takes the form of a wearable electronic device including a housing, a memory, and a processor located in the housing. The wearable electronic device may include three or more sensors, each located in a different region of the housing. Each sensor of the three or more sensors may be configured to generate a measurement of a parameter. The memory may be configured to store instructions, and the processor may be configured to execute the instructions stored in the memory. In response to execution of the instructions by the processor, the processor may be configured to generate an adjusted measurement of a biometric parameter using at least the measurements of the parameter generated by the three or more sensors.

Still another embodiment takes the form of a method. The method may include determining, by a processor of an electronic wearable device, an impact of a condition on skin temperature of a user based on measurement of a parameter using a number of sensors located in a different region in a housing of the electronic wearable device. The method includes determining, by the processor, the skin temperature of the user measured by a sensor of the number of sensors, and generating, by the processor, an adjusted measurement of the skin temperature based on the determined impact of the condition on the skin temperature of the user.

Yet another embodiment takes the form of a wearable electronic device including a housing. The housing may have a front surface, a back surface, and a sidewall disposed between the front surface and the back surface. The wearable electronic device may include a display viewable through the front surface, and a set of temperature sensors that includes a first temperature sensor thermally connected to the back surface, a second temperature sensor thermally connected to the top surface or the sidewall, and a third temperature sensor. The wearable electronic device may also include a temperature monitor. The temperature monitor may be configured to generate a temperature of a user responsive to temperature measurements obtained from the first temperature sensor, the second temperature sensor, and the third temperature sensor.

BRIEF DESCRIPTION OF THE DRAWINGS

Reference will now be made to representative embodiments illustrated in the accompanying figures. It should be understood that the following descriptions are not intended to limit this disclosure to one included embodiment. To the contrary, the disclosure provided herein is intended to cover alternatives, modifications, and equivalents as may be included within the spirit and scope of the described embodiments, and as defined by the appended claims.

FIG. 4B depicts an example flowchart for determining an impact of various conditions on a measurement of a biometric parameter, as described herein.

The use of the same or similar reference numerals in different figures indicates similar, related, or identical items.

Figure 1:
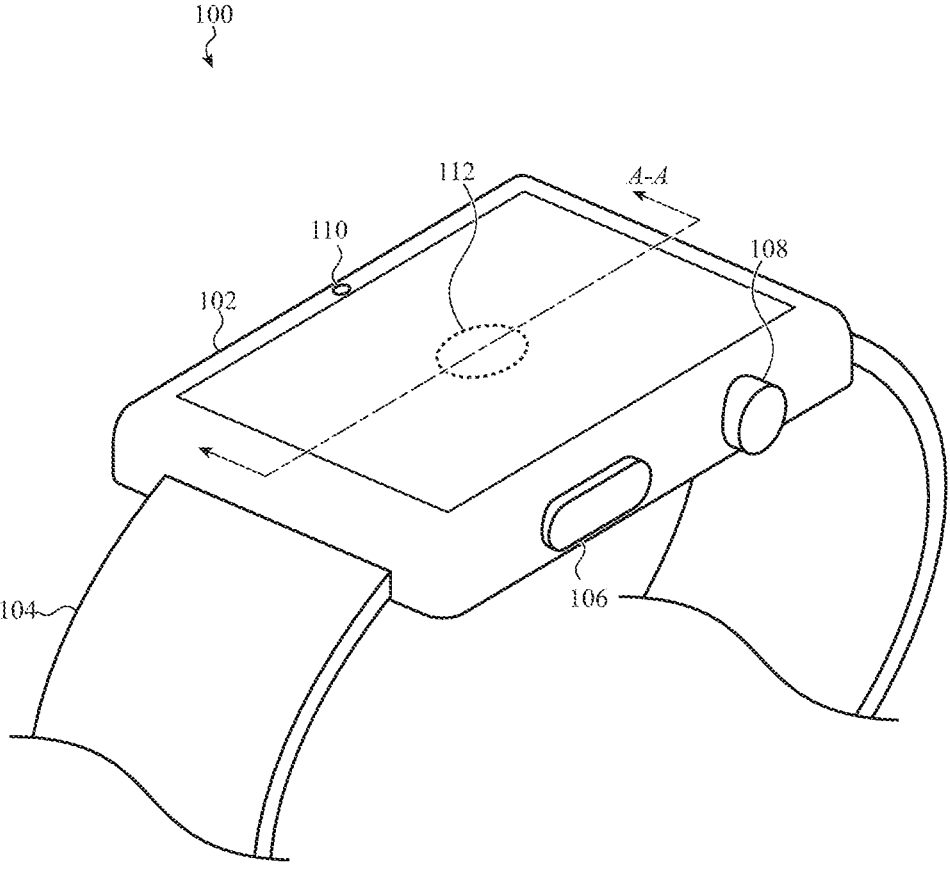
FIG. 1 depicts an example wearable electronic device, as described herein.

Additionally, it should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following description is not intended to limit the embodiments to one preferred embodiment. On the contrary, it is intended to cover alternatives, modifications, and equivalents as can be included within the spirit and scope of the described embodiments as defined by the appended claims.

Embodiments described herein include wearable electronic devices having a number of sensors. A first subset of the number of sensors may be configured to generate a measurement of a biometric parameter, while a second subset of the number of sensors may be configured to measure one or more aspects affecting the measurement of the biometric parameter. Each sensor, which may be a temperature sensor or a thermal sensor, may be selected from multiple types including, but not limited to, a discrete electronic component, an integrated circuit, and/or a thermoelectric material. By exploiting the scalability of integrated circuits, the number of sensors may be flexibly expanded beyond the exact numbers of sensors presented in this disclosure.

By way of a non-limiting example, the biometric parameter may be a temperature of a user of the wearable electronic device. As described herein, the wearable electronic device may determine the temperature of the user using a temperature sensor included in the wearable electronic device. The temperature sensor may be located at or near a bottom of a housing of the wearable electronic device such that the temperature sensor is likely to remain in contact with the body of the user. The temperature measured using a single temperature sensor may not predict an accurate body temperature of the user for various reasons, including, but not limited to, ambient environmental conditions. Accordingly, for improving an accuracy of the measured temperature, an additional sensor may be used to determine an impact of various environmental conditions on the temperature of the user, e.g., a temperature of the skin of the user. In some cases, the additional sensor used for determining the impact of various environmental conditions on the temperature of the user may be positioned on or near a top of the housing.

One or more additional sensors, for example, one or more thermal sensors, may also be used to determine an impact of one or more conditions, such as the heating of various electrical components inside the housing, the thermal conductivity of a material of various components of the wearable electronic device, and a particular style of wearing the wearable electronic device, on a temperature measurement of a user. Additionally, or alternatively, one or more thermal sensors may be positioned in such a way that each thermal sensor is in direct contact with an ambient environment for providing measurements of an ambient temperature. The one or more thermal sensors may have low thermal conductivity, and may thereby be used to factor out an impact that the ambient temperature has on the temperature inside the wearable electronic device.

A network of distributed sensors for measuring the temperature of a user according to various embodiments, as described herein, may avoid a need to thermally isolate one or more sensors from other components of the wearable electronic device (e.g., to obtain a more accurate prediction of the temperature of the user). Instead, a set of temperature measurements may be acquired, some of the measurements may be combined (e.g., averaged), some of the measurements may be used to compute correction coefficients, and so on.

In some embodiments, and as a non-limiting example, an electronic wearable device may be one of a watch, an earbud, and so on. Taking a watch as an example, the watch may have one or more sensors on or near a bottom surface of a housing of the watch. These sensors may remain in contact with the skin of a user who is wearing the watch, or at least have a high likelihood of remaining in contact with the skin of the user. By way of a non-limiting example, the sensors may be in thermal contact with the user's skin through a heat transfer medium (e.g., a crystal or metal surface on the back surface of the watch). Accordingly, the sensors may measure a surface temperature of the user's skin. However, the surface temperature measured by the sensors may not reflect an accurate internal body temperature of the user because the surface temperature measured by the sensors may be affected by various environmental conditions. For example, if the user is sitting in a room having an air-conditioner blowing cold air in the room, the temperature measured by the one or more sensors may generate a temperature measurement that is lower than an actual temperature of the body temperature of the user. Similarly, if the user is in an open environment, the time of the day and weather conditions may impact the temperature measured by the one or more sensors. In other words, if the user's temperature is measured through a heat transfer medium of the watch, an accuracy of the measured temperature may be affected from the environment of the heat transfer medium and/or user.

In addition to environmental or ambient conditions, other factors may lead to an inaccurate temperature measurement of the sensor. By way of a non-limiting example, other factors that may affect a temperature measurement of a user may be the thermal conductivity of a material of one or more components of the wearable electronic device. For example, when a wristband of the electronic wearable device is made of metal, the wristband may have a higher thermal conductivity compared to a wristband that is made of silicone rubber or another material. Thermal conductivity of the wristband may affect temperature measurements made by one or more sensors, for example, while the user is working out, and so on. In some cases, temperature measurements by one or more sensors touching the skin of the user may generate temperature measurements that are lower than the temperature of the user's skin if the user is wearing the watch loosely. And, if the user is wearing the watch tightly, temperature measurements made by one or more sensors touching the skin of the user may generate temperature measurements that are higher than the temperature of the user's skin. In addition, an angle of the wearable electronic device may affect the contact area(s) of one or more sensors positioned against a user's skin and, thereby, affect the accuracy of a predicted skin temperature of the user.

Further, one or more sensors at or near the bottom surface of a housing of a wearable electronic device, and inside the housing, may generate an inaccurate temperature measurement because of heat generated by electrical components inside the housing. Accordingly, for improving the accuracy of the temperature measurement(s) made by one or more sensors touching the body of the user, an additional sensor on the top or sidewall of the housing of the electronic device, and/or near an electrical component generating heat inside the housing of the electronic device, may be used to adjust the temperature measurement(s). Alternatively, the temperature sensor(s) in contact with the user may be thermally isolated from other components of the wearable electronic device, to prevent their temperature measurement(s) from being affected by other factors. However, thermal isolation of the one or more sensors adds complexity to the integration of the sensor(s) into the device.

In some embodiments, the accuracy of the temperature measurement(s) by the temperature sensor(s) in contact with a user's skin may be improved by using a network of sensors in which each sensor in the network is located in a different region of the housing of the wearable electronic device. By way of a non-limiting example, the network of sensors may include a first subset of one or more sensors on or near a bottom surface of a housing of the device, and a second subset of one or more sensors located on a top surface of the housing, on a side surface of the housing, or within an internal cavity formed by the housing. In some cases, the network of sensors may include at least three sensors, with the first subset of sensors including at least one sensor, and the second subset of sensors including at least one sensor. In some cases, a sensor in the second subset of sensors may be disposed on or interior to the housing.

In some embodiments, each sensor in the second subset of temperature sensors may be used to determine a required adjustment to a temperature measured by the first subset of temperature sensors. While measuring the core body temperature of a user using a wearable electronic device, such as a watch, heat flowing through the user's wrist may be sensed or measured by a sensor in the wearable electronic device. However, as heat from the user's body flows to the sensors in the wearable electronic device, differences in material properties within the wearable electronic device may give rise to local heat transport characteristics. The network of sensors, and in particular the second subset of temperature sensors, may provide thermal measurements corresponding to each of a number of distinct thermal paths from the user's wrist to respective sensors in the wearable electronic device. By way of a non-limiting example, and in some embodiments, a sensor in the second subset of temperature sensors may output a common mode signal and a differential mode signal. The common mode signal may provide information from which common characteristics such as contact quality with the user's body, for example, with the user's wrist, may be estimated. The differential mode signal may provide information related to a heat transport characteristic intrinsic to the wearable electronic device. Accordingly, based on an identification of wearing conditions related to the wearable electronic device, ambient conditions, and/or an ambient parameter, certain thermal paths from the user's body to a sensor in the wearable electronic device may be bypassed if a thermal path is determined to be based on a poor thermal contact. By way of a non-liming example, one or more sensors in the network of sensors, for example, from the second subset of temperature sensors, may continue to monitor one or more thermal paths from the user's body to respective sensors in the wearable electronic device, thereby providing a robust measurement for various conditions related to wearing the wearable electronic device, ambient conditions, and/or ambient parameters.

As a non-limiting example, and in some embodiments, a user may be notified of their temperature by displaying the temperature on a display of a wearable electronic device. In addition, or alternatively, a haptic output may be provided to notify a user of a temperature measurement. In some cases, a temperature measurement may be conveyed to a user on another electronic device, using communication circuitry included in the wearable electronic device. For example, the wearable electronic device may send a notification of a user's temperature to a phone of the user, using a Bluetooth, Wi-Fi, 3G, 4G, 5G, and/or other communication protocol or technology.

As described herein, and in accordance with some embodiments, the accuracy of a temperature measurement may be improved because the temperature measurement is adjusted based on measurements from one or more other sensors, based on various external and/or internal conditions of a device. Further, temperature measurement using a network of sensors located in different regions of a device housing may reduce mechanical integration complexity. The mechanical integration complexity may be reduced because one or more sensors inside the housing may not be required to be thermally isolated from other components in the housing which, comparatively, may affect temperature measurement due to internal thermal events such as joule heating of various components like a battery and/or integrated circuits.

In some embodiments, factors affecting temperature measurement of a user may be referred to as "aggressors" in this disclosure. The aggressors may be internal aggressors or external aggressors. For example, components such as a battery or an integrated circuit causing joule heating may be referred to as aggressors. Since a battery or integrated circuit affecting temperature measurement is inside the housing, heating from the battery or the internal circuit may be referred to as an internal aggressor. An aggressor which is outside the housing is referred to herein as an external aggressor. An example of an external aggressor is an environmental condition, such as air conditioning in the room where the user is present, or a style of wearing the wearable electronic device (e.g., tight or loose), and so on.

In some embodiments, a watchdog monitor (also referred herein as a watchdog temperature sensor or a watchdog sensor) may be used to monitor one or more aggressors, and/or estimate thermal aggression onto one or more sensors of the network of temperature sensors. In the present disclosure, the network of temperature sensors, the network of sensors, the network of distributed sensors, and/or the network of a number of sensors may be used to refer to the same entity. If a measurement made by one or more sensors configured to measure an impact of an external aggressor and/or an internal aggressor, on a temperature measurement of a user, exceeds a particular threshold value, the watchdog monitor or the watchdog sensor may cause a process for measuring the temperature of a user to be delayed for a particular time duration. Additionally, or alternatively, measurements from a particular sensor may be discarded for a particular time duration, or measurements using a particular sensor may be delayed for a particular time duration. The particular time duration may be fixed and preconfigured, or the particular time duration may be dynamically selected based on the value of the measured temperature above the particular threshold value. In a case where the measurement(s) made by the one or more sensors do not meet particular threshold values, an aggressor monitor (or watchdog monitor) may be used to accurately compensate for heat flux additions from the aggressor to one or more sensors of the network of temperature sensors. For example, the aggressor heat flux addition may be subtracted from an estimate of physiological heat flux. Thus, the compensation for heat flux addition may increase an aggregate sensor data availability, as measurements made under aggression can also be used, and compensated, instead of being discarded. Further, when no thermal aggression is present, the watchdog monitor may contribute to an improved body temperature estimation.

In some embodiments, thermal isolation may be provided in a region of a housing connecting the housing to a wristband, to improve the accuracy of a temperature measurement of a user by reducing the impact of thermal conductivity of the material used in the wristband. In particular, a region in the housing thermally isolates a sensor of a set of temperature sensors from a component of the wearable electronic device having thermal conductivity above a threshold value.

In some embodiments, and by way of a non-limiting example, an adjusted temperature measurement of the body of the user ($T_c$) may be represented by the following equation: $T_c \approx T_{BC} + \Phi_{BC}$, where $T_{BC}$ may represent a temperature measured by one or more sensors located at a bottom of a housing, which sensor(s) may be in contact with the body of the user, and $\Phi_{BC}$ may represent an estimated impact of a number of aggressors, including internal aggressors and/or external aggressors, on the temperature $T_{BC}$, where $\Phi_{BC}$ may be directly correlated to an actively monitored power consumption of each aggressor to provide a robust estimate of internal thermal aggression under various wearing conditions and/or ambient conditions.

The impact of each individual internal aggressor $T_{agg}$ onto temperatures $T_1$ or $T_2$ measured by two temperature sensors can be modeled as a linear first-order transfer function (H,G) as shown below.

$$H = \frac{T_1}{T_{agg}} \approx \frac{1+as}{1+bs}, \quad G = \frac{T_2}{T_{agg}}$$

While the above Laplace-domain transfer functions represent internal heat dynamics, a change in thermal loading due to a change in wearing conditions and/or ambient conditions may alter H and G. However, H and G may be calibrated, for example, in real time, using simultaneous measurements of one or more temperature measurements ($T_1$, $T_2$) from one or more temperature sensors, and one or more temperature measurements from one or more watchdog monitors ($T_{agg}$), while an aggressor is detected. For example, a self-calibration may be performed and/or periodically repeated after detecting a change in wearing conditions and/or ambient conditions by another subsystem, which for example may include, but is not limited to, an accelerometer, a skin impedance sensor, a pressure sensor, and so on, within the wearable electronic device. Accordingly, upon noticing no change in wearing conditions and/or ambient conditions for some time, H and G may be assumed to be fixed, and a total error in core body temperature measurement ($\Delta T_c$) due to n internal thermal aggressors may be calculated using the following equation.

$$\Delta T_c = (1+\alpha_0) \cdot \Delta T_1 - \alpha \Delta T_2 = (1+\alpha_0)\Sigma_n \alpha_n \cdot H_n \cdot T_{agg,n} - \alpha \Sigma_n \beta_n \cdot G_n \cdot T_{agg,n}$$

In some embodiments, a watchdog monitor may be positioned near each aggressor. For example, a watchdog monitor may be positioned near each aggressor in a wearable electronic device having a large number of internal aggressors. Weighing factors $\alpha$ and $\beta$ may then be assigned to each aggressor, favoring watchdog measurements that are situated closer to the respective aggressor, and exhibit lower measurement noise. As a result, a Kalman filter corresponding to the wearable electronic device may be constructed, which also minimizes the total mean squared error of $T_c$. Accordingly, in the cases where $\Delta T_c$ can be determined with a high accuracy, $\Delta T_c$ may be applied to determine the temperature of the body of the user ($T_c$). Otherwise, the data can be discarded until $\Delta T_c$ is below a particular threshold value.

In some embodiments, data information collected from the network of temperature sensors may be used to generate one or more metrics. For example, information collected from the network of temperature sensors, particularly variations in the temperature measurements of one or more sensors in contact with the user's body, may be used for generating a contact metric identifying, for example, a tilt of the electronic device and/or a tightness of a band, and so on. The generated contact metric may be fed as an input to another type of sensors, for example, a sensor configured to measure a heart rate or a blood oxygen level, and so on.

The foregoing and other embodiments, and various alternatives thereof and variations thereto, are discussed below with reference to FIGS. 1-6 for purposes of explanation, and to facilitate an understanding of various configurations and constructions of a system, such as described herein. However, it will be apparent to one skilled in the art that some of the specific details presented herein may not be required in order to practice a particular described embodiment, or an equivalent thereof.

FIG. 1 depicts an example wearable electronic device, as described herein. By way of a non-limiting example, the wearable electronic device 100 may be a watch and include a housing 102 and a wristband 104. The wearable electronic device may have one or more of a button 106 and a crown 108. The one or more of a button 106 may be configured, for example, to select a menu item and/or power cycle of the wearable electronic device, and so on. The crown 108 may be configured to be rotatable and/or pressable to scroll through the menu, to adjust time and/or configuration, and so on. As shown in FIG. 1, the wearable electronic device 100 may include a first sensor 112 located on a bottom surface of the housing 102, and a second sensor 110 located on a top surface of the housing 102. Each of the first sensor 112 and the second sensor 110 may be configured to measure a parameter, such as a temperature. In some embodiments, thermal isolation may be provided in a region of the housing 102 connecting the housing 102 to the wristband 104, to improve the accuracy of a temperature measurement of a user by reducing the impact of thermal conductivity of the material used in the wristband 104. In particular, a region in the housing 102 may thermally isolate a sensor of a set of temperature sensors from a component of the wearable electronic device 100 having thermal conductivity above a threshold value. A watchdog monitor, described herein according to some embodiments, may be located inside the housing 102 near one or more heat generating components. The one or more heat generating components may include, but are not limited to, a circuitry 204, a processor, an optical sensor, and so on.

In some embodiments, the parameter being measured by the first sensor 112 may be a body temperature of the user and the parameter being measured by the second sensor 110 may be a temperature of an external aggressor or an internal aggressor that can affect the body temperature of the user wearing the wearable electronic device 100.

As shown in FIG. 1, the wearable electronic device 100 may be a watch, and, therefore, the first sensor 112 located at the bottom of the housing 102 of the wearable electronic device may remain in contact with the body of the user. Accordingly, in some embodiments, the first sensor 112 may be configured to measure a temperature of the user body as measured at the contact surface, i.e., skin of the user.

However, as discussed above, the temperature measured using a single temperature sensor, for example, the first sensor 112, may not predict an accurate body temperature of the user for various reasons, including, but not limited to, ambient environmental conditions. Accordingly, for improving an accuracy of the measured temperature, one or more additional sensors may be used. In FIG. 1, only one additional sensor, a second sensor 110, is shown. However, more than one additional sensor may be used to determine an impact of other factors, such as an environment in which the user is present, on the temperature measurement of the first sensor 112.

In some embodiments, the second sensor 110 may be located on the top of the housing 102. The second sensor 110 thus is not in direct contact with the body of the user. Accordingly, the second sensor 110 may be used to determine an impact of various environmental conditions on the temperature measurement by the first sensor 112 on the surface body of the user, e.g., skin of the user.

By way of a non-limiting example, temperature measurement in the wearable electronic device may be represented by the following equation: $T_c=T_1+\alpha(T_1-T_2)$, where $T_c$ represents temperature of the body of the user, and $T_1$ and $T_2$ represent temperature measured by the first sensor 112 and the second sensor 110, respectively. The variable $\alpha$ represents a correction coefficient that is applied to the difference of $T_1$ and $T_2$ by which the temperature $T_1$ measured by the first sensor 112 may be affected by various conditions described above, such as environmental conditions, thermal conductivity of the material of the wristband, and so on. In some cases, the value of the variable $\alpha$ may vary by 100%, which may cause the temperature $T_{wrist}$ to have a variance of approximately −10 degree Celsius.

Accordingly, various embodiments as described below may improve an accuracy of the temperature measured by the first sensor 112.

Figure 2:
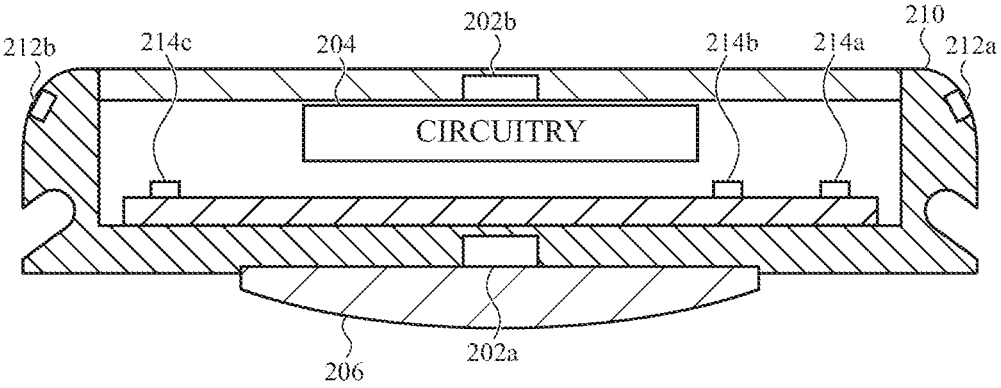
FIG. 2 depicts a cross-section view of an example wearable electronic device, as described herein.

FIG. 2 depicts a cross-section view of an example wearable electronic device, in accordance with some embodiments. As shown in FIG. 2, the wearable electronic device 100 has a first sensor 202a and a second sensor 202b. The first sensor 202a may be similar to the first sensor 112 and the second sensor 202b may be similar to the second sensor 110. Accordingly, the first sensor 202a may be located on a bottom surface of the housing 210 and remain in contact with the skin of the user. The first sensor 202a may, therefore, measure the temperature of the body of the user.

In some embodiments, a network of sensors may include a first subset of sensors configured to measure a body temperature of the user and a second subset of sensors configured to measure an impact of external and/or internal aggressors on the temperature measurement by one or more sensors of the first subset of sensors. Accordingly, there may be more than one sensor like the first sensor 202a configured to measure the body temperature of the user. Each sensor of the first subset of sensors may be located in different regions near the bottom surface of the housing, and may be positioned for likely contact with a user's body, e.g., skin. By using more than one sensor in the first subset of sensors and averaging a temperature measurement of each sensor of the first subset of sensors, impact of a localized hotspot on the user's body on the temperature measurement by a particular temperature sensor may be avoided.

As described above, the second sensor 202b may determine an impact on the measurement of temperature by the first sensor due to ambient conditions. By way of a non-limiting example, the ambient conditions may include external temperature conditions. If the user is in a room with an air conditioner on, the lower room temperature may also affect the temperature measurement of the first sensor 202a, which is thermally coupled with the body of the user.

In some embodiments, in addition to the second sensor 202b, additional sensors may be used to improve an accuracy of the temperature measured by the first sensor 202a. As shown in FIG. 2, sensors 212a and 212b may be located on the sidewall or side surface of the housing 210. The additional sensors 212a and 212b may thus be used to determine an impact of various external conditions on the temperature measurement by the first sensor 202a. As described above, the sensors 202b, 212a, and 212b may thus be considered part of the second subset of sensors configured to measure the impact of external aggressors on the temperature measurement by the first sensor 202a.

In addition to the external aggressors, internal aggressors may also affect the temperature measurement by the first sensor 202a. Sensors 214a, 214b, and 214c, inside the housing 210, may be used to compensate the internal aggressors affecting the temperature measurement by the first sensor 202a. The sensors 214a, 214b, and 214c may thus be used to determine impact on the temperature measurement due to internal aggressors, such as heating of the internal components of the housing 210 due to the electrical current flowing through the circuitry 204 or power consumption by the circuitry 204. The sensors 214a, 214b, and 214c may thus be considered part of the second subset of the sensors. By way of a non-limiting example, the sensors 214a, 214b, and/or 214c may also act as a watchdog sensor, as described herein in accordance with some embodiments.

As shown in FIG. 2, a network of a number of sensors, particularly, three or more sensors distributed in different regions of the housing 210, may improve the accuracy of the temperature measurement by the first sensor 202a, which is thermally coupled with the body of the user.

In some embodiments, each sensor in the network of the distributed sensor, based on its location in the housing 210, may determine how an external and/or internal aggressor may affect the temperature measurement by the first sensor 202a. For example, sensors 212a and 212b being located on the sidewall of the housing 210 and in the proximity of the locations on the housing 210 where the wristband 104 is connected, may determine how thermal conductivity of the wristband may affect the temperature measurement of the first sensor 202a.

Sensors 212a and 212b, along with the second sensor 202b being located on the top surface of the housing 210 and/or sidewall of the housing 210, may be used to identify an impact on the measurement by the first sensor 202a based on the difference in measurement of each of the sensors 212a, 212b, and 202b. For example, if the user is sitting in a room right under an air conditioning vent, the air blowing from the vent above the user may affect the temperature measurement of the sensor 202b more than the temperature measurements of the sensors 212a and 212b. Accordingly, differences between temperature measurements of the sensors 212a, 212b, and/or 202b may be used to identify an adjustment of temperature measurement by each of the sensors 212a, 212b, and/or 202b. The sensors 212a and 212b may be located on a side surface of the housing 210 and may be configured to measure external and/or internal aggressors based on their location in the housing 210.

As shown in FIG. 2, in some embodiments, a back cover 206 of the housing 210 may remain in contact with the body of the user. The back cover 206 may include thermally conductive material, such as glass, crystal, metal, and so on. Accordingly, the first sensor 202a may measure body temperature of the user through the back cover 206.

In the sections below, an algorithm or a process of determining how to compensate temperature measurement of each sensor of the network of distributed temperature sensors, for various external and/or internal aggressors and to determine an adjusted or corrected temperature of the first sensor 202a, is described. The first sensor 202a may in some cases be used to make an initial (uncorrected) measurement of a basal body temperature of the user.

Figure 3:
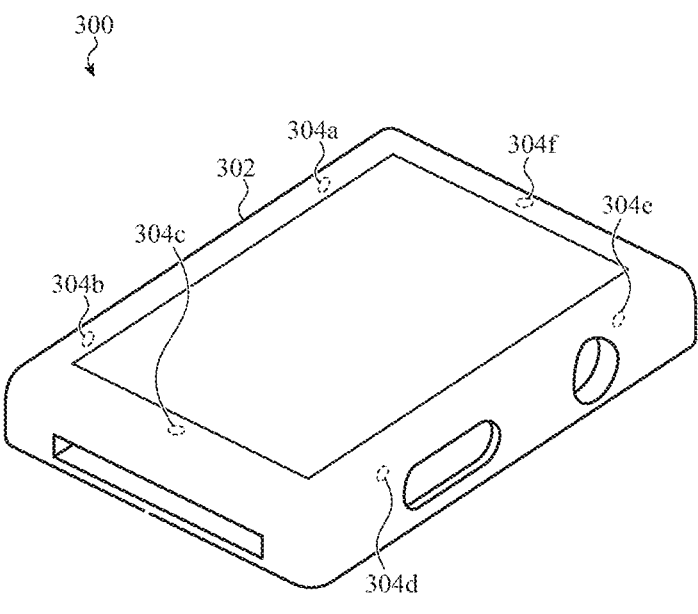
FIG. 3 depicts an example wearable electronic device having a network of distributed sensors, as described herein.

FIG. 3 depicts an example wearable electronic device having a network of distributed sensors, such as described herein, in accordance with some embodiments. As shown in FIG. 3, a wearable electronic device 300 may include a housing 302 with a number of sensors, for example, temperature sensors 304a, 304b, 304c, 304d, 304e, and 304f located on a top surface and/or sidewall of the housing 302. A temperature sensor may be located on a bottom surface of the housing 302, which remains in contact with the skin of the user and measure body temperature of the user. Temperature measurements by sensors 304a through 304f may determine an impact of the external and/or internal aggressors on the temperature measurement by the temperature sensor measuring the body temperature of the user. In some embodiments, one or more temperature sensors may be located inside the housing 302. The one or more sensors located inside the housing 302 may determine the impact of heating of components internal to the housing 302. Accordingly, a network of distributed sensors located in different regions of the housing 302 may be used to generate a corrected temperature measured by the temperature sensor at the bottom surface of housing 302.

Figure 4A:
FIG. 4A depicts an example flowchart for measuring a biometric parameter such as a skin temperature, as described herein.
Figure 4A:
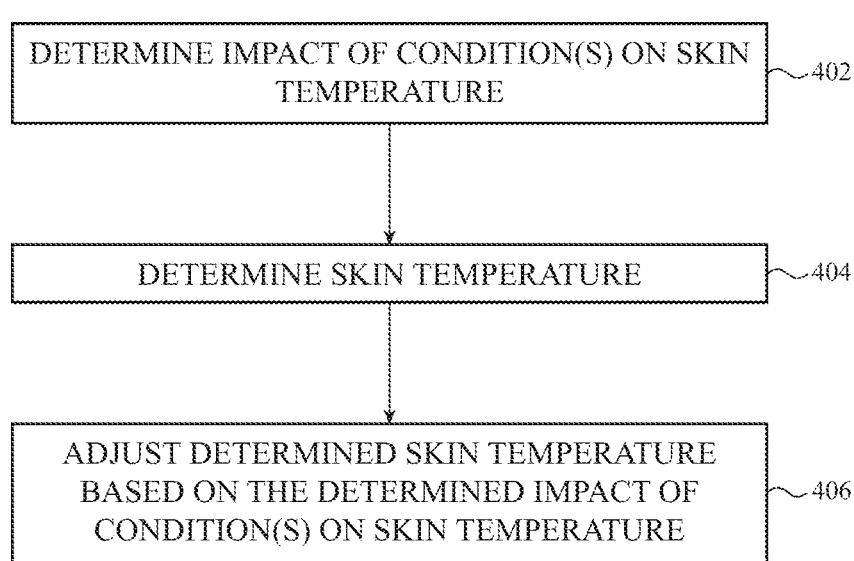

FIG. 4A depicts an example flowchart for measuring a biometric parameter and FIG. 4B depicts an example flowchart for determining an impact of various conditions on a measurement of a biometric parameter The embodiments are described herein with reference to a measurement of temperature, but the described techniques are also relevant to measurement of other types of parameters. As shown in the flowchart 400a, at 402, an impact of various conditions on a skin temperature of a user may be measured. As described above, the various conditions that may affect temperature measurement of the first sensor 202a may be referred to as aggressors. The aggressors may include external aggressors or internal aggressors.

By way of a non-limiting example, the external aggressors may include environmental conditions in which the user is present. For example, if the user is sitting in a room, with an air conditioner on, the temperature measurement by the first sensor 202a may be lower compared to the actual body temperature of the user. Other external aggressors may include the thermal conductivity of a material used in a wristband or other components of the wearable electronic device. In some embodiments, the wearable electronic device may be a watch, and if the user is wearing the watch tightly, an increased thermal coupling between the first sensor 202a and the body of the user may affect the temperature measurement. Similarly, a spatial position of the watch on the user's body, such as an angle of the watch face, the user's physical activity, and/or an alignment of the watch with a surface at which a temperature is measured may affect the temperature measurement by the first sensor 202a.

By way of a non-limiting example, the internal aggressors may be joule heating of the electrical components inside the housing of the wearable electronic device.

At 404, a temperature may be determined by the first sensor 202a, which is in contact with the user's body. The temperature measured by the first sensor 202a may not represent an accurate temperature due to external and/or internal aggressors that affect the temperature measurement of the first sensor 202a. Accordingly, the temperature measured by the first sensor 202a may be adjusted at 406 based on the impact of external and/or internal aggressors, as described herein, using FIG. 4B.

By way of a non-limiting example, the adjusted temperature of a user may be determined based on the equation below:

$T_c = T_1 + \alpha_1(T_1 - T_2) + \alpha_2(T_1 - T_3) + \ldots + \alpha_n(T_1 - T_n)$, where, $T_c$ may represent an adjusted temperature of the body of the user; $T_1, T_2, \ldots, T_n$ may represent temperature measured by various sensors located in different regions of the housing, and $\alpha_1, \alpha_2, \ldots, \alpha_n$ may represent correction coefficient values corresponding to each sensor determined as described herein with reference to FIG. 4B.

In some embodiments, an equation based on a different formula may be used to determine the adjusted temperature of the user. For example, an adjusted temperature measurement of the body of the user ($T_c$) may be determined using an equation: $T_c \approx T_{BC} + \Phi_{BC}$, where $T_{BC}$ may represent a temperature measured by one or more sensors located at a bottom of the housing 102, which sensor(s) may be in contact with the body of the user, and $\Phi_{BC}$ may represent an estimated impact of a number of aggressors, including internal aggressors and/or external aggressors, on the temperature $T_{BC}$, where $\Phi_{BC}$ may be directly correlated to an actively monitored power consumption of each aggressor to provide a robust estimate of internal thermal aggression under various wearing conditions and/or ambient conditions.

As described herein, an impact of each individual internal aggressor $T_{agg}$ onto temperatures $T_1$ or $T_2$ measured by two temperature sensors can be modeled as linear first-order transfer functions (H,G) as shown below.

$$H = \frac{T_1}{T_{agg}} \approx \frac{1 + as}{1 + bs}, \quad G = \frac{T_2}{T_{agg}}$$

While the above Laplace-domain transfer functions may represent internal heat dynamics, a change in thermal loading due to a change in wearing conditions and/or ambient conditions may alter H and G. However, H and G may be calibrated, for example, in real time, using simultaneous measurements of one or more temperature measurements ($T_1$, $T_2$) from one or more temperature sensors, and one or more temperature measurements from one or more watchdog monitors ($T_{gg}$), while an aggressor is detected. For example, a self-calibration may be performed and/or periodically repeated after detecting a change in wearing conditions and/or ambient conditions by another subsystem, which for example may include, but is not limited to, an accelerometer, a skin impedance sensor, a pressure sensor, and so on, within the wearable electronic device. Accordingly, upon noticing no change in wearing conditions and/or ambient conditions for some time, H and G may be assumed to be fixed, and a total error in core body temperature measurement ($\Delta T_c$) due to n internal thermal aggressors may be calculated using the following equation.

$\Delta T_c = (1 + \alpha_0) \cdot \Delta T_1 - \alpha \Delta T_2 = (1 + \alpha_0) \Sigma_n \alpha_n \cdot H_n \cdot T_{agg,n} - \alpha \Sigma_n \beta_n \cdot G_n \cdot T_{agg,n}$ In some embodiments, a watchdog monitor may be positioned near each aggressor. For example, a watchdog monitor may be positioned near each aggressor in a wearable electronic device having a large number of internal aggressors. Weighing factors $\alpha$ and $\beta$ may then be assigned to each aggressor, favoring watchdog measurements that are situated closer to the respective aggressor, and exhibiting lower measurement noise. As a result, a Kalman filter corresponding to the wearable electronic device may be constructed, which also minimizes the total mean squared error of $T_c$. Accordingly, in the cases where $\Delta T_c$ can be determined with a high accuracy, $\Delta T_c$ may be applied to determine the temperature of the body of the user ($T_c$). Otherwise, the data can be discarded until $\Delta T_c$ is below a particular threshold value.

Accordingly, the embodiments described herein may generate an adjusted temperature measurement with higher accuracy.

In some embodiments, the adjusted temperature of the body of the user may be displayed to the user on a display screen of the wearable electronic device. By way of a non-limiting example, the adjusted temperature of the body of the user may be reported to the user as a haptic output using a haptic output circuitry of the wearable electronic device. The adjusted temperature of the body may also be reported to the user using a communication module of the wearable electronic device to another electronic device. For example, the adjusted temperature may be reported to a phone of the user using a Wi-Fi, Bluetooth, 3G, 4G, 5G, and/or another communication protocol. The adjusted temperature may be reported to an application server. The application server may store the reported adjusted temperature data in a database, for various applications, such as ovulation prediction.

In some cases, when an aggressor affecting temperature measurement does not meet specified conditions, the user may be notified to move to a more ideal measuring environment. For example, if the user is working in a cold storage area, the temperature in the cold storage area may affect the temperature measurement of one or more sensors beyond a specific threshold. The user may then be notified to move to a more ideal measuring environment, such as to move to a different location that is not too cold.

In some embodiments, the adjusted temperature may be calculated at a particular time period and logged locally or in another device, locally or remotely connected with the wearable electronic device 100 for later use.

Reference is now made to FIG. 4B that depicts an example flowchart for determining impact on measurement of temperature, as described herein, in accordance with some embodiments. As shown in the flowchart 400b, at 408, impact of external aggressors, such as environmental conditions, on temperature measurement of one or more sensors located on a top surface and/or sidewall of a housing of the wearable electronic device may be determined. The wearable electronic device may be subjected to various types of environmental conditions, and through measurement test data collected from the one or more sensors, a correction coefficient value for adjustment of temperature measurement for one or more sensors of the wearable electronic device may be determined. By way of a non-limiting example, the correction coefficient value for the adjustment of temperature measurement may be determined using a machine-learning model.

In some embodiments, by way of a non-limiting example, the various types of environmental conditions may include ambient temperature conditions, altitude of a location, humidity, and so on.

In some embodiments, at 410, impact of internal aggressors on temperature measurement by a sensor inside the housing of the wearable electronic device may be determined. The wearable electronic device may include electrical components, and a battery to provide a required power supply to the electrical components. The electrical components may produce heat due to an electrical current flowing through them and/or power consumption. The heat generated thus may affect temperature measurement of one or more sensors. Accordingly, to compensate for the internal aggressors, a correction coefficient may be determined for adjustment of temperature measurement of the sensor for compensating for the joule heating of the components inside the housing. The correction coefficient value may be determined for one or more sensors based on temperature measurement data corresponding to the heat generated by the components when various combinations of applications are running on the wearable electronic device.

In some embodiments, at 412, impact of thermal conductivity of material used in one or more components of the wearable electronic device may be determined for adjustment of the temperature measurement. As described above, a wrist band made of metal may have a higher thermal conductivity compared to a wrist band of rubber or fabric. Similarly, the material used for the housing may also affect temperature measurement. Accordingly, the thermal conductivity of one or more components of the wearable electronic device may affect the temperature measurement. A correction coefficient value may be determined to compensate for temperature adjustment for one or more sensors due to the thermal conductivity of the one or more components of the wearable electronic device.

At 414, an effect of spatial placement of the wearable electronic device on temperature measurement may be determined. As described above, a watch worn tightly may increase thermal coupling between the wearable electronic device and the body of the user. Further, an alignment of the wearable electronic device with a surface at which a temperature is measured may also affect thermal coupling between the wearable electronic device and the body of the user. Accordingly, using one or more sensors, the spatial position of the wearable electronic device with reference to the body of the user may be determined. A correction coefficient value to adjust the temperature measurement for one or more sensors may be determined using test measurement data. As described above, a machine-learning algorithm may be used to perform any of the steps described herein.

Figure 5:
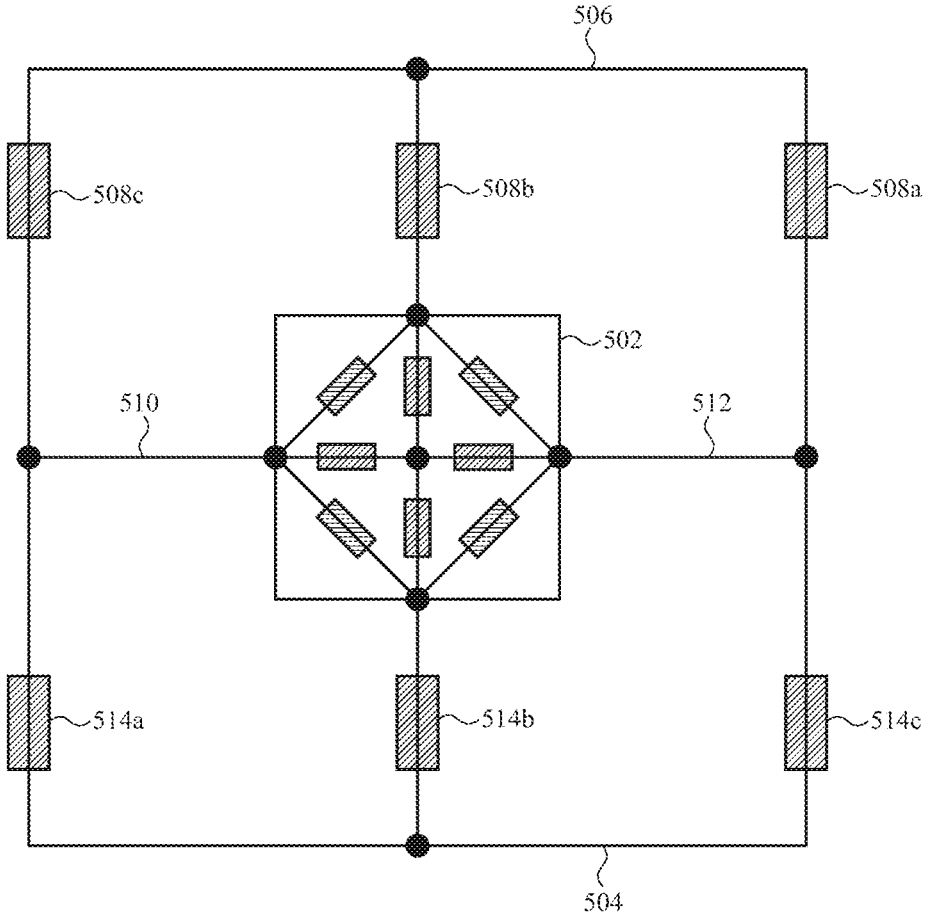
FIG. 5 depicts a schematic diagram of an example wearable electronic device having a network of distributed sensors, as described herein.

FIG. 5 depicts a schematic diagram of an example wearable electronic device having a network of distributed sensors, such as described herein, in accordance with some embodiments. A wearable electronic device 502 may include one or more sensors 514a, 514b, and/or 514c to measure a temperature of a user 504. One or more sensors 508a, 508b, and/or 508c may be used to measure an impact of ambient conditions 506 on the temperature measurement made by one or more sensors 514a, 514b, and/or 514c. The wearable electronic device 502 may have a housing 512. Accordingly, one or more sensors of 514a, 514b, and/or 514c may be on the bottom surface of the housing 512, and one or more sensors of 508a, 508b, and/or 508c may be on the top surface or sidewall of the housing 512. The wearable electronic device may include a wristband 510. Accordingly, the components shown in FIG. 5 may be thermally coupled with each other. The embodiments described herein may thus be used for adjusted temperature measurement using a network of temperature sensors distributed in different regions of the housing.

Figure 6:
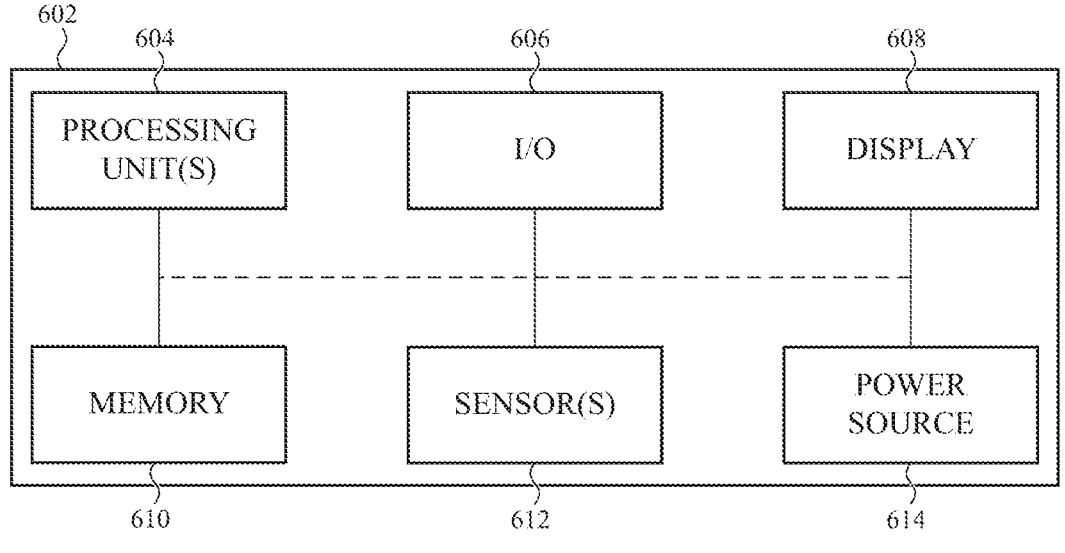
FIG. 6 describes an example electrical block diagram of a wearable electronic device, as described herein.

FIG. 6 depicts an example block diagram of the wearable electronic device described herein, in accordance with some embodiments. The wearable electronic device 602 may include one or more processing units 604, an input/output mechanism 606 (e.g., an input/output device, an input/output port, a button, a haptic output interface, or the combination thereof), a display 608 (e.g., a light-emitting display), a memory 610 or a storage device, one or more sensors 612, and a power source 614. By way of a non-limiting example, the input/output mechanism may include a communication module to communicate with another electronic device and/or an application server using a Wi-Fi, Bluetooth, 3G, 4G, 5G, and/or another communication protocol, and so on. The one or more processing units 604 can communicate, either directly or indirectly, with some or all of the components of the wearable electronic device 602. For example, a system bus or other communication mechanism can provide communication between the one or more processing units 604, the power source 614, the memory 610, the one or more sensors 612, the input/output mechanism 606, and the display 608.

The one or more processing units 604 may be implemented as any electronic device capable of processing, receiving, or transmitting data or instructions. By way of a non-limiting example, the one or more processing units 604 may be a microcontroller, a microprocessor, a central processing unit (CPU), an application-specific integrated circuit (ASIC), an integrated circuit (IC), a field-programmable gate array (FPGA), a digital signal processor (DSP), and/or a system-on-chip (SOC), and so on. Accordingly, the term "processing unit" is meant to encompass a single processor or processing unit, multiple processors, multiple processing units, or other suitably configured computing element or elements.

In some embodiments, various components of the wearable electronic device 602 may be controlled by multiple processing units. For example, select components of the wearable electronic device 602 (e.g., a sensor 612) may be controlled by a first processing unit and other components of the wearable electronic device 602 (e.g., the display 608) may be controlled by a second processing unit, where the first and second processing units may or may not be in communication with each other.

By way of a non-limiting example, in some embodiments, an input may be processed through a number of processing units. Each processing unit of the number of processing units may process the received input according to the instructions set corresponding to that processing unit, and then may forward or send a command to other processing units for further processing.

In some embodiments, the power source 614 may be implemented with any device capable of providing energy to the wearable electronic device 602. For example, the power source 614 may be one or more batteries or rechargeable batteries. By way of a non-limiting example, the power source 614 may be a power connector or power cord that connects the wearable electronic device 602 to another power source, such as a wall outlet.

In some embodiments, the memory 610 may store electronic data that may be used by the wearable electronic device 602. For example, the memory 610 may store electrical data or content such as, for example, software instructions, algorithms, audio and video files, documents and applications, device settings and user preferences, timing signals, control signals, and data structures or databases. The memory 610 may be configured as any type of memory. By way of a non-limiting example, the memory 610 may be implemented as random access memory (RAM), read-only memory (ROM), static random-access memory (SRAM), Flash memory, removable memory, and/or a hard disk, and so on.

In some embodiments, the wearable electronic device 602 may include one or more sensors 612 positioned almost anywhere on the wearable electronic device 602. The one or more sensors 612 may be configured to sense one or more types of parameters, which by way of a non-limiting example may include temperature, pressure, light, touch, movement, relative motion, and/or biometric data (e.g., biological parameters), and so on. By way of a non-limiting example, in some embodiments, the one or more sensors 612 may include a force sensor, a temperature sensor, a position sensor, a light or optical sensor, an accelerometer, a pressure transducer, a gyroscope, a magnetometer, a health monitoring sensor, and so on. In some embodiments, the force sensor may be implemented as a strain gauge. Additionally, the one or more sensors 612 may utilize any suitable sensing technology, including, but not limited to, capacitive, ultrasonic, resistive, optical, ultrasound, piezoelectric, and thermal sensing technology.

In some embodiments, the I/O mechanism 606 may transmit and/or receive data from a user or another electronic device. An I/O device may include a display, a touch sensing input surface, one or more buttons (e.g., a graphical user interface "home" button, a physical button such as a tact switch button, and/or a bongo button), one or more cameras, one or more microphones or speakers, one or more ports such as a microphone port, and/or a keyboard. In some embodiments, by way of a non-limiting example, an I/O device or port can transmit electronic signals via a communications network, such as a wireless and/or wired network connection. Examples of wireless and wired network connections include, but are not limited to, cellular, Wi-Fi, Bluetooth, IR, and Ethernet connections.

Further, various embodiments in the present disclosure are described using a watch as an example of a wearable electronic device, but other types of wearable electronic devices, such as hearing aids, medical devices (for example, glucose monitors), lifestyle devices (for example, personal communication devices, visual aids, and/or smart clothing) may also be used. By way of a non-limiting example, the watch may serve as a hub or central connection interface to wirelessly connect to a network of external temperature sensing devices distributed over the body of the user (for example, hearing aids, glucose monitors, visual aids, personal communication devices, smart closing [clothing?], and so on).

As used herein, the phrase "at least one of" preceding a series of items, with the term "and" or "or" to separate any of the items, modifies the list as a whole, rather than each member of the list. The phrase "at least one of" does not require selection of at least one of each item listed; rather, the phrase allows a meaning that includes at a minimum one of any of the items, and/or at a minimum one of any combination of the items, and/or at a minimum one of each of the items. By way of example, the phrases "at least one of A, B, and C" or "at least one of A, B, or C" each refer to only A, only B, or only C; any combination of A, B, and C; and/or one or more of each of A, B, and C. Similarly, it may be appreciated that an order of elements presented for a conjunctive or disjunctive list provided herein should not be construed as limiting the disclosure to only that order provided.

One may appreciate that although many embodiments are disclosed above, that the operations and steps presented with respect to methods and techniques described herein are meant as exemplary and accordingly are not exhaustive. One may further appreciate that alternate step order or fewer or additional operations may be required or desired for particular embodiments.

Although the disclosure above is described in terms of various exemplary embodiments and implementations, it should be understood that the various features, aspects, and functionality described in one or more of the individual embodiments are not limited in their applicability to the particular embodiment with which they are described, but instead can be applied, alone or in various combinations, to one or more of the some embodiments of the invention, whether or not such embodiments are described and whether or not such features are presented as being a part of a described embodiment. Thus, the breadth and scope of the present invention should not be limited by any of the above-described exemplary embodiments but is instead defined by the claims herein presented.

The present disclosure recognizes that personal information data, including biometric data, such as a body temperature, in the present technology, can be used to the benefit of users. For example, the use of biometric authentication data can be used for convenient access to device features without the use of passwords. In other examples, user biometric data is collected for providing users with feedback about their health or fitness levels. Further, other uses for personal information data, including biometric data, that benefit the user are also contemplated by the present disclosure.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure, including the use of data encryption and security methods that meets or exceeds industry or government standards. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates embodiments in which users selectively block the use of, or access to, personal information data, including biometric data. That is, the present disclosure contemplates that hardware and/or software elements can be provided to prevent or block access to such personal information data. For example, in the case of biometric authentication methods, the present technology can be configured to allow users to optionally bypass biometric authentication steps by providing secure information such as passwords, personal identification numbers (PINS), touch gestures, or other authentication methods, alone or in combination, known to those of skill in the art. In another example, users can select to remove, disable, or restrict access to certain health-related applications collecting users' personal health or fitness data.

In addition, it is understood that organizations and/or entities responsible for the access, aggregation, validation, analysis, disclosure, transfer, storage, or other use of private data such as described herein will preferably comply with published and industry-established privacy, data, and network security policies and practices. For example, it is understood that data and/or information obtained from remote or local data sources, only on informed consent of the subject of that data and/or information, should be accessed aggregated only for legitimate, agreed-upon, and reasonable uses.

Example computing resources contemplated herein include, but are not limited to: single or multi-core processors; single or multi-thread processors; purpose-configured co-processors (e.g., graphics processing units, motion processing units, sensor processing units, and the like); volatile or non-volatile memory; application-specific integrated circuits; field-programmable gate arrays; input/output devices and systems and components thereof (e.g., keyboards, mice, trackpads, generic human interface devices, video cameras, microphones, speakers, and the like); networking appliances and systems and components thereof (e.g., routers, switches, firewalls, packet shapers, content filters, network interface controllers or cards, access points, modems, and the like); embedded devices and systems and components thereof (e.g., system(s)-on-chip, Internet-of-Things devices, and the like); industrial control or automation devices and systems and components thereof (e.g., programmable logic controllers, programmable relays, supervisory control and data acquisition controllers, discrete controllers, and the like); vehicle or aeronautical control devices and systems and components thereof (e.g., navigation devices, safety devices or controllers, security devices, and the like); corporate or business infrastructure devices or appliances (e.g., private branch exchange devices, voice-over internet protocol hosts and controllers, end-user terminals, and the like); personal electronic devices and systems and components thereof (e.g., cellular phones, tablet computers, desktop computers, laptop computers, wearable devices); personal electronic devices and accessories thereof (e.g., peripheral input devices, wearable devices, implantable devices, medical devices and so on); and so on. It may be appreciated that the foregoing examples are not exhaustive.

As described herein, the term "processor" refers to any software and/or hardware-implemented data processing device or circuit physically and/or structurally configured to instantiate one or more classes or objects that are purpose-configured to perform specific transformations of data including operations represented as code and/or instructions included in a program that can be stored within, and accessed from, a memory. This term is meant to encompass a single processor or processing unit, multiple processors, multiple processing units, analog or digital circuits, or other suitably configured computing element or combination of elements.

What is claimed is:

1. A wearable electronic device, comprising:
a housing;
a memory located in the housing, the memory configured to store instructions;
a processor located in the housing, the processor configured to execute the instructions stored in the memory;
a watchdog sensor located inside the housing near one or more heat generating components inside the housing; and
three or more sensors, each configured to generate a measurement of a parameter and each sensor of the three or more sensors located in a different region in the housing;
wherein, in response to the execution of the instructions by the processor, the processor is configured to:
delay measurement by a sensor of the three or more sensors for a particular period in response to a temperature measured by the watchdog sensor exceeding a particular threshold value; and generate an adjusted measurement of a biometric parameter using at least measurements of the parameter generated by the three or more sensors and the watchdog sensor.

2. The wearable electronic device of claim 1, wherein the parameter is a temperature, and the biometric parameter is a body temperature of a user.

3. The wearable electronic device of claim 1, wherein to generate the adjusted measurement of the biometric parameter, the processor is further configured to:

determine a correction coefficient, based on one or more aspects, for a subset of sensors of the three or more sensors, wherein the biometric parameter is a body temperature of a user.

4. The wearable electronic device of claim 3, wherein the correction coefficient is determined based on the one or more aspects comprising one or more of: an environmental condition, a spatial position of the wearable electronic device on the user, an alignment of the wearable electronic device with a surface at which the body temperature is measured, and conductivity of material of one or more components of the wearable electronic device.

5. The wearable electronic device of claim 1, wherein the wearable electronic device is a watch.

6. The wearable electronic device of claim 1, wherein a region in the housing thermally isolates a sensor of the three or more sensors from a component of the wearable electronic device having thermal conductivity above a threshold value.

7. The wearable electronic device of claim 1, wherein a first sensor of the three or more sensors is located at a bottom of the housing, a second sensor of the three or more sensors is located at a top of the housing, and a third sensor of the three or more sensors is located on a side surface of the housing.

8. The wearable electronic device of claim 7, wherein the side surface is a first side surface, and wherein a fourth sensor of the three or more sensors is located on a second side surface of the housing, opposite the first side surface.

9. The wearable electronic device of claim 1, wherein to generate the adjusted measurement of the biometric parameter, the processor is further configured to:

determine a correction coefficient based on a machine-learning algorithm trained using data associated with one or more measurements of the parameter from each sensor of the three or more sensors based on a number of aspects comprising one or more of: an environmental condition, a spatial position of the wearable electronic device on a user, an alignment of the wearable electronic device with a surface at which a temperature is measured, and conductivity of material of one or more components of the wearable electronic device.

10. The wearable electronic device of claim 1, further comprising a display mounted within the housing and configured to display a notification of the adjusted measurement of the biometric parameter to a user.

11. A method, comprising:

determining, by a processor of a wearable electronic device, an impact of at least one condition on a skin temperature of a user, the determining performed by measuring ambient temperature using two or more sensors in a set of three or more sensors located in different regions of a housing of the wearable electronic device and a temperature measured by a watchdog sensor, the watchdog sensor located inside the housing near one or more heat generating components; and determining, by the processor, the skin temperature of the user, the skin temperature determined by measuring a temperature using a third sensor in the set of three or more sensors; and in response to the temperature measured by the watchdog sensor exceeding a particular threshold value, excluding, by the processor, a measurement of a temperature by a sensor located inside the housing based on proximity of the sensor from the one or more heat generating components inside the housing; and generating, by the processor, an adjusted measurement of the skin temperature based on the determined impact of the at least one condition on the skin temperature of the user.

12. The method of claim 11, wherein a region in the housing thermally isolates a sensor of the set of three or more sensors from a component of the wearable electronic device having thermal conductivity above a threshold value.

13. The method of claim 11, wherein the skin temperature of the user is measured by a sensor located at a bottom of the housing, and wherein the impact of the at least one condition on the skin temperature of the user is measured by two or more sensors of the set of three or more sensors located on a top surface of the housing, a side surface of the housing, or inside the housing.

14. The method of claim 11, wherein determining the impact on the at least one condition impacting the skin temperature of the user comprises determining the impact of the at least one condition impacting the skin temperature of the user based on one or more aspects comprising one or more of: an environmental condition, a spatial position of the wearable electronic device on the user, an alignment of the wearable electronic device with a surface at which the skin temperature is measured, a spatial position of a sensor in the housing of the wearable electronic device, and a thermal conductivity of material of one or more components of the wearable electronic device.

15. The method of claim 11, further comprising:

providing a notification of an adjusted measurement of the skin temperature of the user comprises generating a haptic output corresponding to the adjusted measurement of the skin temperature of the user.

16. A wearable electronic device, comprising:

a housing having a front surface, a back surface, and a sidewall disposed between the front surface and the back surface;

a display viewable through the front surface;

a set of temperature sensors comprising:

a first temperature sensor thermally connected to the back surface and positioned to measure a body temperature;

a second temperature sensor thermally connected to one of the front surface or the sidewall and positioned to measure a first ambient temperature; and a third temperature sensor positioned to measure a second ambient temperature;

a watchdog sensor located inside the housing near one or more heat generating components within the housing; and a temperature monitor configured to generate a temperature of a user based on the measured body temperature, first ambient temperature, second ambient temperature, and temperature measured by the watchdog sensor and delay a measurement by a sensor of the set of temperature sensors for a particular period in response to a temperature measured by the watchdog sensor exceeding a particular threshold value.

17. The wearable electronic device of claim 16, further comprising a communication module, wherein the temperature monitor is further configured to:

determine a correction coefficient for each sensor of the set of temperature sensors based on one or more aspects comprising one or more of: an environmental condition, a spatial position of the wearable electronic device on the user, an alignment of the wearable electronic device with a surface at which the temperature is measured, and conductivity of material of one or more components of the wearable electronic device; and provide, on another wearable electronic device, a notification of the temperature of the user using the communication module.

\* \* \* \* \*